United States Patent
Walter

(10) Patent No.: US 8,256,332 B2
(45) Date of Patent: Sep. 4, 2012

(54) METHOD FOR AUTOMATICALLY FEEDING A SPECIMEN TO BE THINLY CUT TO THE KNIFE OF A MICROTOME

(75) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 410 days.

(21) Appl. No.: 12/600,362

(22) PCT Filed: Apr. 17, 2008

(86) PCT No.: PCT/DE2008/000660
§ 371 (c)(1), (2), (4) Date: Nov. 16, 2009

(87) PCT Pub. No.: WO2008/141599
PCT Pub. Date: Nov. 27, 2008

(65) Prior Publication Data
US 2010/0147120 A1  Jun. 17, 2010

(30) Foreign Application Priority Data
May 19, 2007 (DE) .......................... 10 2007 023 457

(51) Int. Cl.
B26D 7/06 (2006.01)
(52) U.S. Cl. ............................ 83/76.8; 83/915.5; 83/703
(58) Field of Classification Search ................ 83/13, 39, 83/56, 72, 75.5, 364, 365, 367, 370, 703, 83/714–719, 915.5
See application file for complete search history.

(56) References Cited

U.S. PATENT DOCUMENTS

| | | | | |
|---|---|---|---|---|
| 3,688,500 A | * | 9/1972 | Chancel et al. | 60/431 |
| 4,239,963 A | * | 12/1980 | August et al. | 73/514.26 |
| 4,377,958 A | * | 3/1983 | Leighton | 83/410.7 |
| 4,566,225 A | * | 1/1986 | Bizot et al. | 451/6 |
| 4,731,733 A | * | 3/1988 | Knoll | 700/56 |
| 4,966,460 A | * | 10/1990 | Kahley | 356/640 |

(Continued)

FOREIGN PATENT DOCUMENTS
DE  4205256 C2  6/1993

OTHER PUBLICATIONS
WIPO, Written Opinion of the International Search Authority, PCT/DE2008/000660, Nov. 19, 2009.

*Primary Examiner* — Sean Michalski
(74) *Attorney, Agent, or Firm* — Hodgson Russ LLP

(57) ABSTRACT

A method for the automatic and contact-free relative approach between a specimen (6) and a knife (7) of a microtome (1). A first light beam bundle (9') forms a detector-side zero point and a last light beam bundle (9") forms a detector-side end point of a light band (8), the light band (8) being arranged perpendicular to the second spatial direction (Y) and in the direction thereof spaced from the knife, a zero point ($X_0$) being assigned to a reference position of the knife blade ($X_{Blade}$). The specimen (6) is guided through the light band (8) by way of a cutting movement. The position of the highest point of the specimen ($X_{Specimen}$) in the first spatial direction (X) is determined from the number of shaded light beam bundles (9).

8 Claims, 2 Drawing Sheets

U.S. PATENT DOCUMENTS

| | | | |
|---|---|---|---|
| 5,043,907 A * | 8/1991 | Richards | 700/167 |
| 5,067,379 A * | 11/1991 | Butler et al. | 83/13 |
| 5,226,335 A * | 7/1993 | Sitte et al. | 83/74 |
| 5,287,759 A * | 2/1994 | Kaneda | 73/865.8 |
| 5,309,223 A * | 5/1994 | Konicek et al. | 356/621 |
| 5,461,953 A * | 10/1995 | McCormick | 83/36 |
| 5,535,654 A * | 7/1996 | Niesporek et al. | 83/364 |
| 5,761,977 A * | 6/1998 | Jakobi et al. | 83/13 |
| 5,850,772 A * | 12/1998 | Hayashi | 83/37 |
| 5,860,349 A * | 1/1999 | Takeda | 83/881 |
| 5,906,148 A * | 5/1999 | Aihara et al. | 83/72 |
| 5,985,217 A * | 11/1999 | Krulevitch et al. | 422/536 |
| 5,995,230 A * | 11/1999 | Madlener et al. | 356/614 |
| 6,041,686 A * | 3/2000 | Lihl et al. | 83/628 |
| 6,105,483 A * | 8/2000 | Takeda | 83/881 |
| 6,202,488 B1 * | 3/2001 | Cash | 73/514.26 |
| 6,330,348 B1 * | 12/2001 | Kerschmann et al. | 382/128 |
| 6,387,653 B1 | 5/2002 | Voneiff et al. | |
| 6,568,307 B1 * | 5/2003 | Gunther et al. | 83/367 |
| 6,628,408 B1 * | 9/2003 | Franklin et al. | 356/623 |
| 6,869,006 B2 * | 3/2005 | Franklin et al. | 228/1.1 |
| 8,051,760 B2 * | 11/2011 | Walter | 83/713 |
| 8,056,456 B2 * | 11/2011 | Walter | 83/76.8 |
| 8,104,389 B2 * | 1/2012 | Tanki et al. | 83/651 |
| 2002/0020266 A1 * | 2/2002 | Smith | 83/75 |
| 2004/0124378 A1 * | 7/2004 | Lihl et al. | 250/559.12 |
| 2004/0178371 A1 | 9/2004 | Lihl et al. | |
| 2004/0239024 A1 | 12/2004 | Thiem | |
| 2006/0037454 A1 * | 2/2006 | Hess | 83/575 |
| 2006/0119908 A1 * | 6/2006 | Harris et al. | 358/514 |
| 2006/0145101 A1 * | 7/2006 | De Coi | 250/559.12 |
| 2007/0095188 A1 * | 5/2007 | Lang et al. | 83/651 |
| 2007/0177162 A1 * | 8/2007 | Glueck | 356/621 |
| 2008/0072722 A1 * | 3/2008 | Tanki et al. | 83/74 |
| 2008/0094640 A1 * | 4/2008 | Cordingley et al. | 356/614 |
| 2008/0278099 A1 * | 11/2008 | Bergfors et al. | 315/307 |
| 2008/0286859 A1 | 11/2008 | Walter | |
| 2009/0165627 A1 * | 7/2009 | Walter | 83/713 |
| 2009/0244551 A1 * | 10/2009 | Lutz | 356/630 |
| 2010/0179690 A1 * | 7/2010 | Matthias et al. | 700/253 |

* cited by examiner

METHOD FOR AUTOMATICALLY FEEDING A SPECIMEN TO BE THINLY CUT TO THE KNIFE OF A MICROTOME

The invention relates to a method for automatically feeding a specimen to be thinly cut to the knife of a microtome according to the preamble of claim 1.

In the operation of microtomes, it is routinely necessary to position the specimen to be cut exactly with respect to the knife in an accurately positioned and rapid fashion. In this so-called feed operation, care must be taken that neither the knife nor the specimen is damaged. Therefore, it is necessary to prevent inadvertent contact from occurring between the knife and the specimen. Thus, it has been common practice for a long time in the context of the feed operation between the knife and the specimen to observe the approach between the specimen and the cutting edge of the knife through a stereomicroscope. This observation does not always, however, result in a reliable estimate of the spacing between the specimen and the cutting edge. Therefore, also technical feeding aids have continued to be used for a long time, for example a base-mounted illumination system, with which it is possible to illuminate a gap between the knife and the specimen and, on the basis of the width of the illuminated gap, to allow a better evaluation of the spacing between the specimen and the cutting edge. The surface of the specimen to be cut is, however, irregularly shaped before the first cut so that this action, too, only partially achieves the goal.

In addition, when changing the specimen a relatively large distance is set between the knife and the specimen for safety reasons. For this purpose, the feed drive is moved into an end position. When a specimen to be cut first approaches the knife, thus a relatively long distance has to be covered. Since in most cases, the distance between the specimen and the knife is unknown, the travel speed is kept correspondingly low in order to avoid inadvertent collisions of the specimen with the knife.

It is desirable to accelerate the first advance and, in doing so, to replace the error-prone manual or visual evaluation of the spacing between specimen and cutting edge by an automatic faster first advance and, at the same time, to avoid an inadvertent contact between the specimen and the cutting edge before the first cutting operation.

In order to avoid an inadvertent collision between the object and the cutting edge, it is known to arrange sensors in the travel path which, upon response, switch off the feed drive.

From German patent application DE 42 05 256 A1 it is known to arrange, as a sensor, a microswitch with an associated release lug in the travel path between the object and the knife, which microswitch, upon response, switches off the feed drive. Such an arrangement, however, has to be very delicately designed due to the little space in the feed area. This, however, has proved disadvantageous since during the on-going cutting operation cut specimen material is collected at the microtome which can block the delicate arrangement.

Thus, a safe switching of the sensor is not guaranteed.

From WO 00/62035 A1 a microtome with an automatic operational sequence is known. The sample embedded in a cassette is provided with an individual identification code, is automatically taken out of a supply magazine by means of a laterally operating slide device, similar to a slide projector, and is mounted on a sample holder on the feed mechanism. The feed mechanism feeds the sample to the knife of the microtome in a manner not described in more detail. The required amount of thin sections is produced and deposited on a slide. Afterwards, the cassette is removed from the sample holder and stored in a reservoir. The thin sections present on the slide are further prepared and successively image-analytically evaluated. It is not apparent how the samples are automatically advanced.

From German Patent DE 102 58 555 B4, a method and a system for automatically feeding and cutting a specimen in a microtome are known. The surface of the specimen first has to be trimmed in a trimming apparatus, while, at the same time, the distance between the trimmed surface of the specimen and the specimen holder is determined and is transferred to the microtome by a transfer device. Thereafter, the specimen holder is inserted into a microtome receptacle which is oscillated. For producing thin sections, the knife holder is fed to the oscillating specimen holder in defined steps. Contaminations in the specimen holder receptacle of the microtome or mix-ups when changing between the trimming apparatus and the microtome and thus associated malfunctions with respect to the distance determination cannot be excluded.

From DE 199 11 173 C2, a microtome having a motorized feed drive system is known, in which with the aid of a pressure-sensitive sensor by way of a stepwise feeding of the sample the position of the feed drive system is stored when the sensor is switched. The position determined in this way is then used for determining and setting the position of the cut object relative to the cutting plane. Contaminations on the tactile sensor surface can have a negative influence on the measurement result and reduce the positioning accuracy.

From DE 102 58 553 B4, a method for automatically feeding a specimen to a knife of a microtome is known, in which between the knife and the specimen a light barrier is arranged. The specimen has to perform an upward and downward movement during the feed movement until the light barrier is interrupted by the specimen, and thereafter, a switch is made to another feed speed. Until the light barrier is interrupted, the feed movement has to be performed in several steps and is therefore slow. The distance between the light barrier and the knife has to be known and must be re-determined after a knife change. If this is not done, malfunctions due to inaccurate knowledge of the distance between the light barrier and the knife cannot be avoided.

Therefore, it was the object of the invention to overcome the disadvantages of the known methods for automatically feeding specimens in microtomes, to accelerate the feed, to allow, at the same time, an accurate feed of the specimen to the knife of the microtome even after a knife change or a specimen change and to avoid associated malfunctions.

This object is solved according to the invention by a method having the characterizing features of claim 1. Advantageous embodiments of the invention result from the features of the further claims.

The inventive method is characterized in that for the automatic and contact-free feeding of a specimen which is fixed in a specimen holder and is to be brought close to a knife of a microtome at first the highest point of the specimen is determined.

The specimen holder is mounted on a drive unit for generating a relative motion between the knife and the specimen. The drive unit is part of the microtome and drives the specimen holder relative to the knife holder for performing a coarse and section thickness feed movement in a first spatial direction. In this way, the specimen is moved towards the knife. Of course, it is likewise possible in the inventive method to drive the knife for performing the coarse and section thickness feed movement relative to the specimen holder in the first spatial direction for generating a relative motion between the knife and the specimen. At the same time, the drive unit performs cutting movements in a second spatial direction perpendicular to the first spatial direction. In a rotary microtome, this cutting movement is comprised of a downward movement in the second spatial direction parallel to a cutting plane. For performing a further cutting movement, subsequently an upward movement in the second spatial direction has to be performed while, at the same time, a feed movement in the first spatial direction is performed. Given a disc microtome, the cutting movement is also comprised of a downward movement in the second spatial direction parallel to the cutting plane. For performing a further cutting movement, the specimen is once again fed to the knife on a circular path.

Between the knife and the specimen a light barrier with transmitter and receiver is arranged, the light beam of which extends parallel to the knife blade. According to the invention, the light barrier is designed as a light band which is comprised of a plurality of light beam bundles that can individually be detected and are arranged parallel to one another in one plane. A detector-side zero point of the light band is formed by a first light beam bundle, and a last light beam bundle forms the detector-side end point of the light band. As soon as an object, for example the specimen, is moved into the light band, the illuminated area at the receiver becomes smaller and can be converted into a length value. When the light band is designed as a light band micrometer, it is possible to determine a very precise length value. The light band is arranged perpendicular to the second spatial direction and in the direction thereof spaced from the knife blade and stationarily with respect to the microtome. The zero point of the light band is assigned to a reference position of the knife blade. When the knife or the knife holder is moved towards the specimen for generating the coarse and section thickness feed movement, the light band is advantageously arranged stationarily on the knife holder perpendicular to the second spatial direction.

The position of the highest point of the specimen in the first spatial direction is determined in that the specimen is guided through the light band by way of a cutting movement. The specimen shades one or more light beam bundles in the area of the detector-side end point when passing through the light band. The number of shaded light beam bundles is determined metrologically and in this way the position of the highest point of the specimen in the first spatial direction is determined.

When starting the microtome, after a knife change or generally given changes in the relation between knife or knife holder and light band, the reference position of the knife blade in the first spatial direction and with respect to the zero point of the light band has to be determined for a precise automatic advance during the later operation. For this purpose, a test specimen, for example a paraffin block, is fed to the knife in steps of predetermined section thickness while performing cutting movements. With every cutting movement, the position of the highest point of the specimen is determined from the number of shaded light beam bundles of the light band. As soon as sections are removed from the test specimen by means of the knife, the position of the highest point of the test specimen with respect to the last cutting movement does no longer change. The position determined in this way is defined as the reference position of the knife blade.

For the automatic production of sections, a specimen to be cut is fed to the microtome in a specimen holder. After successful determination of the highest point of the new specimen and in knowledge of the reference position of the knife blade, for accelerating the production of sections, the specimen holder is then fed in a coarse feed movement by the value of the difference between the highest point of the specimen and the reference position of the knife blade in a rapid movement in the first spatial direction, and afterwards a cutting operation with predetermined cutting speed is performed. Provided that the drive unit is comprised of a so-called micrometer mechanism, the rapid feeding of the specimen can be performed advantageously without steady cutting movements in one single operation. Steady cutting movements with, at the same time, a rapid feeding are the cause for undesired oscillations of the entire microtome, which are to be avoided. After the rapid feeding has been performed, it is switched over to the section thickness feed, and the thin section production can be started straight away.

It is likewise possible, given a corresponding design of the light band as a light band micrometer and its fast evaluation, to monitor the position of the highest point of the specimen permanently given a rapid feeding and to switch-over to the section thickness feed systematically in front of the reference position of the knife blade. In this way, a complex micrometer mechanism in the drive unit can be dispensed with.

Advantageously, after the rapid coarse feeding, at first also cutting operations with larger feed steps performed once or several times as trimming steps can be carried out for creating a planar cutting surface. This serves for a further automation of the work flow since additional external devices for performing trimming cuts can be dispensed with. Uneven specimen surfaces are monitored with the aid of the light band and further trimming cuts are performed for as long as during the entire section production no more changes are determined at the light band on the detector-side.

Further, according to the invention, during a cutting movement a cutting window can automatically be set in that an interruption of a light beam bundle caused by the specimen during a cutting movement and a subsequent uncovering of a light beam bundle of the light band is used for encoding an encoder in the drive unit. For example, this can trigger an incremental encoder integrated in the drive unit for the cutting movement and, on the basis of the counted increments, the length or extension of the specimen in cutting direction can be determined and thus a cutting window can be set. The closer the light band is arranged with respect to the knife edge in the first spatial direction, the more accurate the cutting window is set.

Alternatively, it is likewise possible to automatically set a cutting window during a cutting movement in that a temporary interruption caused by the specimen during a cutting movement up to the subsequent uncovering of a light beam bundle of the light band is used in connection with the predetermined and known cutting speed.

In a further embodiment of the invention, a faster return speed deviating from the predetermined cutting speed is automatically chosen after the determination of the cutting window. The knowledge about the cutting window can be used particularly advantageously in a disc microtome in that after a cut has been performed, a switch to a faster rotational speed is made up to the next beginning of a cutting window. In this way, the specimen throughput or, the production of sections is further increased.

Further advantages and embodiments of the method result from the drawing and are exemplarily described in the following with reference to a rotary microtome schematically illustrated in the Figures.

Figure 1:
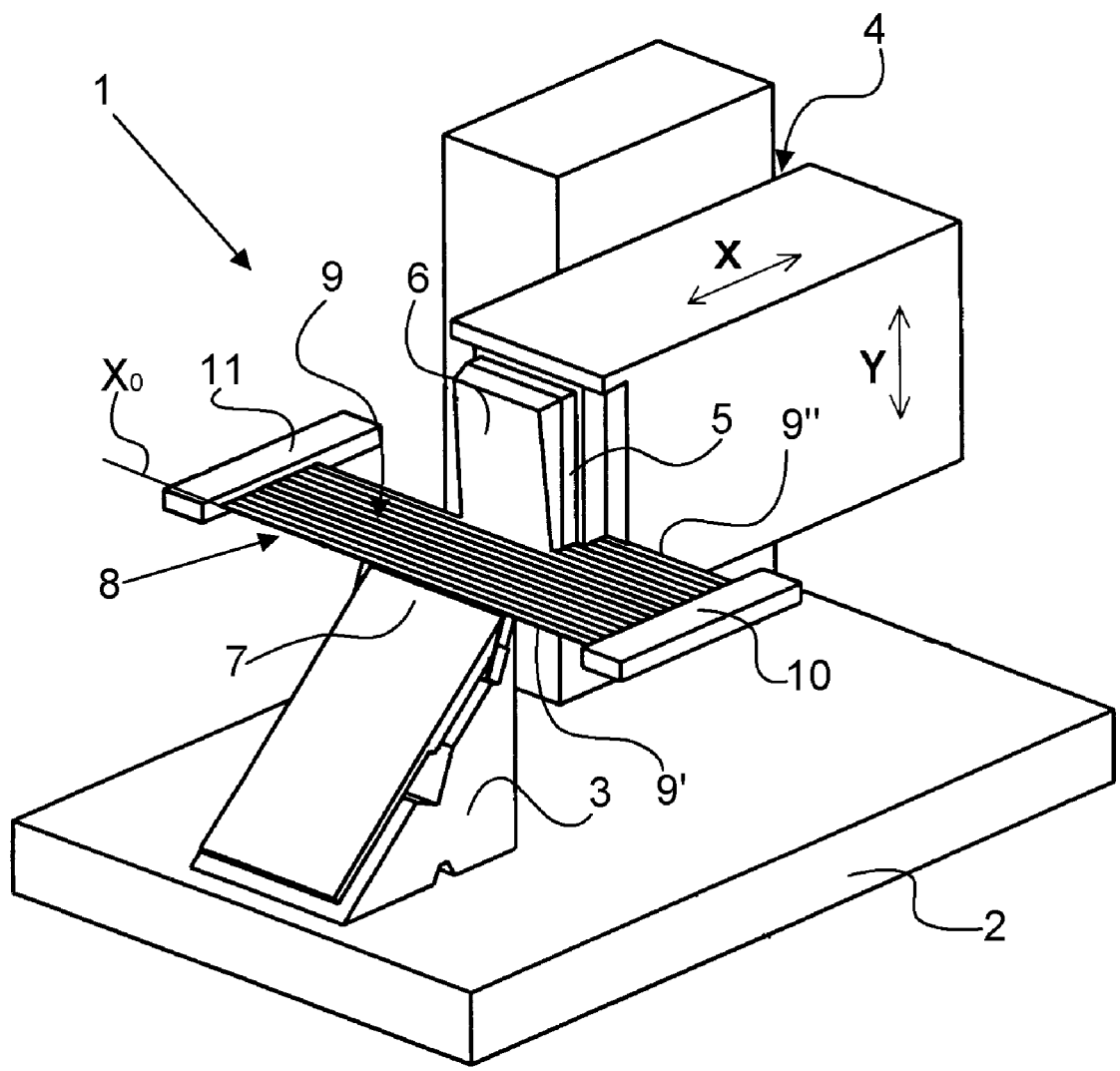
FIG. 1 shows a microtome for cutting specimens with a light band that is set up for performing the method.

FIG. 1 shows in an overview a schematically illustrated rotary microtome 1. On a base plate 2, a knife holder 3 and a drive unit 4 are arranged. On the drive unit 4, a specimen holder 5 in which a specimen 6 to be thinly cut is fixed is provided in the front area facing the knife holder 3. The drive unit 4 moves the specimen 6 in a first spatial direction referenced with X, the so-called feed movement, towards a knife 7 fixed in the knife holder 3. Above the knife holder 3, a light band 8 comprising several light beam bundles 9 which are arranged parallel to one another in one plane is arranged. The light beam bundles 9 run parallel to a knife blade which is covered by the light band and therefore not illustrated in more detail in FIG. 1. On the one side of the light band 8, there is a transmitter unit 10 and on its other side there is a receiver unit 11. The transmitter unit 10 generates the light beam bundles 9 with, preferably, a short wavelength and is, for example, comprised of gallium nitride LEDs which emit a stable and uniform light with little interference and offer a high local resolution. The receiver unit 11 has a telecentric optical system not illustrated in more detail which only uses parallel light for the image formation. In this way, variations in the lens magnification as a result of a change in the position of the specimen are avoided. As a light receiver not illustrated in more detail, preferably a high speed linear CCD is used which, given a uniform illumination, allows for an extremely high scanning speed. A first light beam bundle 9' facing the knife holder 3 forms the detector-side zero point $X_0$, and a last light beam bundle 9" facing the specimen holder 5 forms the detector-side end point of the light band 8. In this way, a precise length measuring system effective in the first spatial direction X is realized.

Figure 2A:
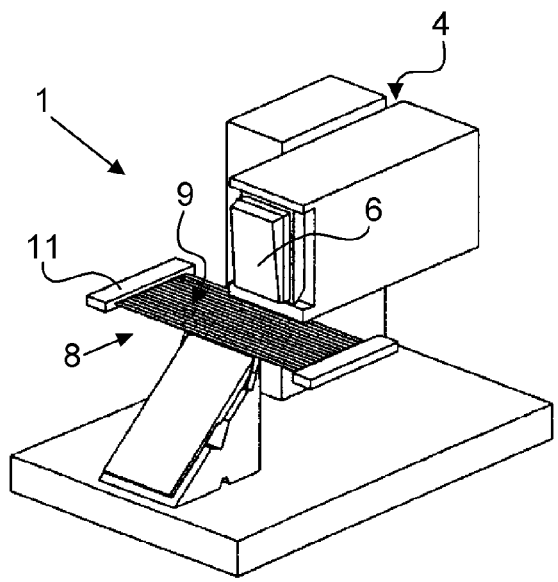
FIG. 2a shows a microtome with a specimen before the beginning of the cutting movement.
Figure 2B:
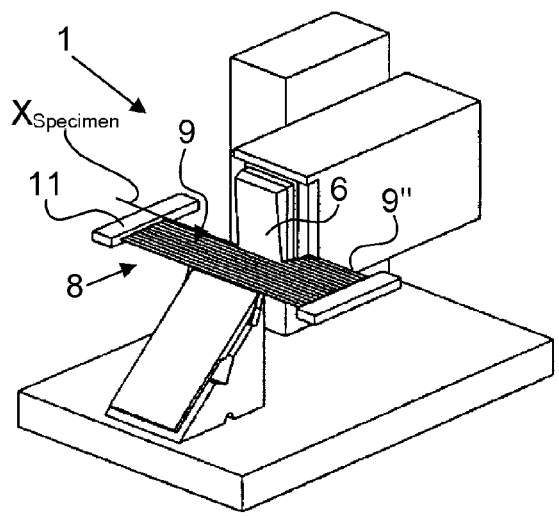
FIG. 2b shows a microtome during the cutting movement.
Figure 2C:
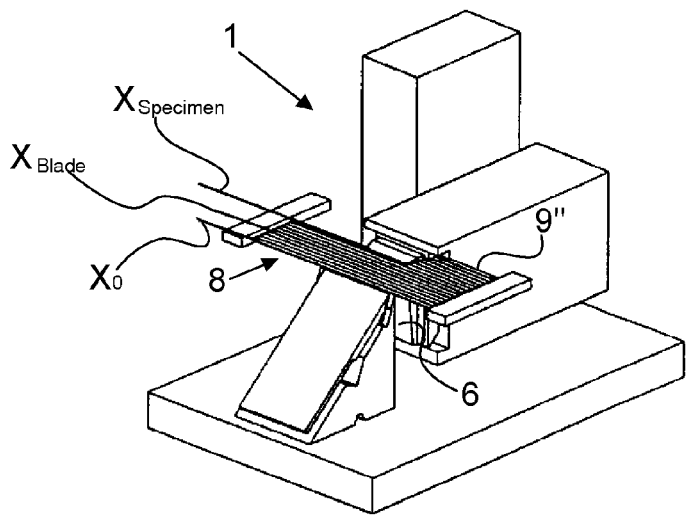
FIG. 2c shows a microtome shortly before the end of the cutting movement.

The method states of FIGS. 2a to 2c illustrated in the following with respect to the embodiment according to FIG. 1, show how, by using the inventive light band, all device and operating parameters necessary for implementing the method such as the degree of specimen feed or a cutting window determination can quickly and automatically be determined.

To this end, FIG. 2a shows for illustration of the movement sequences a microtome 1 with a specimen 6 before the beginning of the cutting movement in a starting position of the drive unit 4. At the beginning of the production of sections, the specimen 6 is located above the light band 8 so that none of the light beam bundles 9 is shaded with respect to the receiver unit 11.

FIG. 2b shows a microtome 1 during the cutting movement. The specimen 6 covers with respect to the receiver unit 11 the last light beam bundle 9" and further light beam bundles arranged next to it in the end-side area of the light band 8. In this way, the highest point of the specimen 6 in the first spatial direction X is determined as $X_{Specimen}$.

FIG. 2c shows a microtome 1 shortly before the end of the cutting movement. The specimen 6 is arranged shortly before the point in time when the shaded light beam bundles are again uncovered near the last light beam bundle 9" of the light band 8. Likewise illustrated is the position $X_{Blade}$ of the knife blade not illustrated in more detail with respect to the detector-side zero point $X_0$ of the light band 8. Due to the distance between $X_{Specimen}$ and $X_{Blade}$ no material removal or no thin section production takes place on the specimen 6 in the above described movement sequence.

LIST OF REFERENCE SIGNS 1 rotary microtome
2 base plate
3 knife holder
4 drive unit
5 specimen holder
6 specimen
7 knife
8 light band
9 light beam bundle
9' first light beam bundle
9" last light beam bundle
10 transmitter unit
11 receiver unit
X first spatial direction
Y second spatial direction
$X_0$ detector-side zero point of the light band
$X_{Blade}$ position of the knife blade in the light band
$X_{Specimen}$ position of the specimen in the light band

The invention claimed is:

1. A method for the automatic and contact-free relative approach between a specimen (6) and a knife (7) of a microtome (1), wherein the knife (7) has a knife blade and is fixed in a knife holder (3), and the specimen (6) is fixed in a specimen holder (5) which is mounted on a drive unit (4) for generating a relative motion between the knife (7) and the specimen (6), wherein between the knife (7) and the specimen (6) a light barrier with transmitter and receiver is arranged and a light beam coming from the transmitter runs parallel to the knife blade, characterized in that a) the drive unit (4) drives the specimen holder (5) relative to the knife holder (3) for performing a coarse and section thickness feed movement in a first spatial direction (X) and for performing a cutting movement in a second spatial direction (Y) perpendicular to the first spatial direction (X), b) the light barrier is formed as a light band (8) comprising a plurality of individually detectable light beam bundles (9) which are arranged parallel to one another in one plane, wherein a first light beam bundle (9') forms a detector-side zero point and a last light beam bundle (9") forms a detector-side end point of the light band (8), c) the light band (8) is arranged stationarily perpendicular to the second spatial direction (Y) and in the direction thereof spaced from the knife blade, wherein the zero point ($X_0$) is assigned to a reference position of the knife blade ($X_{Blade}$), and d) the specimen (6) is guided through the light band (8) in the second spatial direction and, from the number of the shaded light beam bundles (9) of the light band (8), the position of the highest point of the specimen ($X_{Specimen}$) in the first spatial direction (X) is determined.

2. The method according to claim 1, characterized in that at the beginning of the operation of the microtome (1) or given changes in the relation of knife (7) or knife holder (3) to the light band (8), the reference position of the knife blade ($X_{Blade}$) in the first spatial direction (X) and with respect to the zero point ($X_0$) of the light band (8) is determined in that a test specimen (6) is fed to the knife (7) in steps of predetermined section thickness while performing cutting movements, wherein during each cutting movement the position of the highest point of the specimen ($X_{Specimen}$) is determined from the number of shaded light beam bundles (9) of the light band (8), and, as soon as this position no longer changes with respect to the last cutting movement, this position is determined as the reference position of the knife blade ($X_{Blade}$).

3. The method according to claim 1, characterized in that after determination of the highest point of the specimen ($X_{Specimen}$) the specimen holder (5) is fed in a coarse feed movement by the value of the difference between the highest point of the specimen ($X_{Specimen}$) and the reference position of the knife blade ($X_{Blade}$) in a rapid movement in the first spatial direction (X), and subsequently a cutting operation with predetermined cutting speed is performed.

4. The method according to claim 3, characterized in that the cutting operation is performed as a trimming cut by way of a larger feed step performed once or several times.

5. The method according to claim 3, characterized in that during a cutting movement a cutting window is automatically set, a temporary interruption caused by the specimen (6) during a cutting movement up to the subsequent uncovering of a light beam bundle (9) of the light band (8) being used in connection with the predetermined cutting speed for determining the cutting window.

6. The method according to claim 1, characterized in that during a cutting movement a cutting window is automatically set, an interruption caused by the specimen (6) during a cutting movement and a subsequent uncovering of a light beam bundle (9) of the light band (8) being used for encoding an encoder in the drive unit (4).

7. The method according to claim 6, characterized in that after determination of the cutting window a faster return speed deviating from the predetermined cutting speed is automatically chosen.

8. The method according to claim 1, wherein the drive unit (4) drives the knife holder (3) relative to the specimen holder (5).

* * * * *